United States Patent
Gao

(10) Patent No.: US 10,881,879 B2
(45) Date of Patent: Jan. 5, 2021

(54) POSITIONING STUD FOR RADIOACTIVE THERAPY AND STEREOTACTIC DEVICE

(71) Applicants: SHENZHEN OUR NEW MEDICAL TECHNOLOGIES DEVELOPMENT CO., LTD., Shenzhen (CN); SMD MEDICAL CO., LTD., Wuhan (CN)

(72) Inventor: Qi Gao, Shenzhen (CN)

(73) Assignees: SHENZHEN OUR NEW MEDICAL TECHNOLOGIES DEVELOPMENT CO., LTD., Shenzhen (CN); SMD MEDICAL CO., LTD., Wuhan (CN)

(*) Notice: Subject to any disclaimer, the term of this patent is extended or adjusted under 35 U.S.C. 154(b) by 0 days.

(21) Appl. No.: 16/480,635

(22) PCT Filed: Jan. 24, 2017

(86) PCT No.: PCT/CN2017/072394
§ 371 (c)(1),
(2) Date: Jul. 24, 2019

(87) PCT Pub. No.: WO2018/137123
PCT Pub. Date: Aug. 2, 2018

(65) Prior Publication Data
US 2019/0351256 A1    Nov. 21, 2019

(51) Int. Cl.
*A61N 5/10*    (2006.01)
(52) U.S. Cl.
CPC ........... *A61N 5/1049* (2013.01); *A61N 5/103* (2013.01); *A61N 2005/1094* (2013.01); *A61N 2005/1098* (2013.01)

(58) Field of Classification Search
CPC .............. A61B 6/00; A61B 2034/102; A61B 2034/2068; A61B 34/20; A61B 1/00; A61N 5/10; A61N 2005/1098; A61N 2005/1007; A61N 2005/1003; A61N 2005/1094; A61N 5/103
See application file for complete search history.

(56) References Cited

U.S. PATENT DOCUMENTS

| 5,849,261 | A | 12/1998 | Dean et al. |
| 6,478,793 | B1* | 11/2002 | Cosman ............. A61B 18/1477 128/898 |
| 8,740,873 | B2 | 6/2014 | Jones et al. |

(Continued)

FOREIGN PATENT DOCUMENTS

| CN | 1186443 A | 7/1998 |
| CN | 101321542 A | 12/2008 |

(Continued)

OTHER PUBLICATIONS

International Search Report and Written Opinion for Application No. PCT/CN2017/072394 dated Oct. 30, 2017.

(Continued)

*Primary Examiner* — Don K Wong
(74) *Attorney, Agent, or Firm* — Marshall, Gerstein & Borun LLP

(57) ABSTRACT

A positioning stud for radioactive therapy includes a stud rod, a stud tip, and an insulating component. The insulating component is connected between the stud rod and the stud tip, and is used to prevent contact between the stud rod and the stud tip.

16 Claims, 4 Drawing Sheets

(56) References Cited

U.S. PATENT DOCUMENTS

2004/0258641 A1   12/2004  Plos et al.
2005/0276377 A1   12/2005  Carol

FOREIGN PATENT DOCUMENTS

| CN | 203227210 U | 10/2013 |
| CN | 205698004U U | 11/2016 |
| CN | 205759156 U | 12/2016 |
| CN | 106621074 A | 5/2017 |
| WO | WO-9929252 A1 | 6/1999 |
| WO | WO-2006039698 A1 | 4/2006 |

OTHER PUBLICATIONS

Office Action, Chinese patent application No. 201780084439.9, dated Aug. 21, 2020.

* cited by examiner

POSITIONING STUD FOR RADIOACTIVE THERAPY AND STEREOTACTIC DEVICE

CROSS-REFERENCE TO RELATED APPLICATION

This application is a national phase entry under 35 USC 371 of International Patent Application No. PCT/CN2017/072394 filed on Jan. 24, 2017, which is incorporated herein by reference in its entirety.

TECHNICAL HELD

The present disclosure relates to the field of radiotherapy devices, and in particular, to a positioning stud for radioactive therapy and a stereotactic device.

BACKGROUND

With the rapid development of computers and image technologies, radiation therapy technologies also continue to mature. Accuracies of precision radiation therapy technologies, such as three-dimensional conformal radiation therapy (3DCRT), intensity modulated radiation therapy (IMRT), image guided radiation therapy (IGRT) and so on, are also becoming higher. In order to ensure that the rays emitted by the radiotherapy devices accurately find the tumor tissues to be treated, it is necessary to fix the positions to be treated of each patient before performing precise radiation therapy, so that the rays can irradiate the targets accurately.

SUMMARY

The technical problem to be solved by the present disclosure is to provide a positioning stud for radioactive therapy and a stereotactic device, which may prevent the positioning stud tip from scalding the skin of a patient when the temperature of the stud tip is too high due to the heat caused by an alternating current generated by the effect of an alternating magnetic field, thereby guaranteeing safety of therapy process.

In order to solve the above technical problem, a technical solution adopted by the present disclosure is to provide a positioning stud for radioactive therapy. The positioning stud includes a stud rod, a stud tip, and an insulating component. The insulating component is connected between the stud rod and the stud tip, and is configured to block contact between the stud rod and the stud tip.

The insulating component is an electrically insulating spacer.

The electrically insulating spacer is connected to the stud rod by bonding, welding or plug-in type, and the electrically insulating spacer is connected to the stud tip by bonding, welding or plug-in type.

Each of two opposite surfaces of the electrically insulating spacer are provided with a first connecting portion, and a surface of the stud rod connected to the electrically insulating spacer is provided with a second connecting portion correspondingly, and a surface of the stud tip connected to the electrically insulating spacer is provided with a second connecting portion correspondingly, and the second connecting portion on the stud rod is connected to a corresponding first connecting portion on the electrically insulating spacer, and a second connecting portion on the stud tip is connected to another corresponding first connecting portion on the electrically insulating spacer.

The first connecting portion is a raised step and/or a recess hole, and the second connecting portion is a corresponding recess hole and/or a corresponding raised step.

The raised step is inserted into the recess hole by an interference fit for their connection.

The raised step is provided with external threads, and the recess hole is provided with internal threads for matching with external threads of the raised step, and the raised step and the recess hole are connected by a thread fit.

The electrically insulating spacer is configured as a hollow pipe; openings at two ends of the hollow pipe are provided with internal threads respectively, and positions where the stud rod and the stud tip are in contact with the electrically insulating spacer are provided with external threads for matching the internal threads of the hollow pipe; both the stud rod and the stud tip are connected to the electrically insulating spacer by a thread fit.

The insulating component is an insulating sleeve or a sleeve, and one end of the stud rod in contact with the insulating component is provided with a raised step or a recess hole, and one end of the stud tip in contact with the insulating component is provided with a recess hole or a raised step correspondingly; the insulating sleeve is sleeved on the raised step, and the raised step sleeved on the insulating component is connected to the recess hole.

The raised step sleeved on the insulating component is connected to the recess hole by an interference fit; or, an outer side of the insulating component is provided with external threads, and the recess hole disposed on the stud rod or the stud tip is provided with internal threads, and the insulating component and the recess hole is connected by a thread fit; an inner side of the insulating component is provided with internal threads, and the raised step disposed on the stud rod or the stud tip is provided with external threads, and the insulating component is connected to the raised step by a thread fit.

An outer side of the stud rod is provided with a connecting member for connection to a stereotactic device.

The connecting member is provided with external threads, and a position where the stereotactic device is connected with the positioning stud is provided to internal threads, and the connecting member connects the positioning stud and the stereotactic device by a thread fit.

The connecting member is a velvet strip or a hook strip of Velcro, and a position where the stereotactic device is connected to the positioning stud is provided with a corresponding hook strip or a corresponding velvet strip of Velcro, so that the positioning stud is connected to the stereotactic device.

The insulating component is made of one of engineering materials of PEEK (Polyether-ether-ketone), PPSU (Polyphenylene sulfone resins) or ceramic.

In order to solve the above technical problem, a technical solution adopted by the present disclosure is to provide a stereotactic device. The stereotactic device includes a positioning connection frame, and at least two positioning studs according to the Foregoing aspect. The at least two positioning studs are fixedly connected to the positioning connection frame.

The positioning connection frame includes at least two sliding rails having a same number as the at least two positioning studs, each sliding rail is vertically disposed on a plane of the positioning connection frame, each sliding rail is connected to a sliding block which is able to slide along the sliding rail, and each positioning stud is fixedly connected to a corresponding sliding block.

The sliding block is provided with a screw hole, and the screw hole is connected to a stud rod of a corresponding positioning stud by a thread fit.

Different from the prior art, the positioning stud for radioactive therapy of the present disclosure includes a stud rod, a stud tip, and an insulating component; the insulating component is connected between the stud rod and the stud tip, and is used to prevent contact between the stud rod and the stud tip. According to the present disclosure, it is possible to prevent the positioning stud tip from scalding the skin of a patient when the temperature of the stud tip is too high due to the heat caused by an alternating current generated by the effect of an alternating magnetic field, thereby guaranteeing the safety of the therapy process.

DETAILED DESCRIPTION

The technical solutions of the present disclosure are described in detail below with reference to the embodiments. Obviously, the described embodiments are merely some but not all of embodiments of the present disclosure. All other embodiments made on the basis of the embodiments of the present disclosure by a person of ordinary skill in the art without paying any creative effort shall be included in the protection scope of the present disclosure.

A stereotactic positioning stud is a component that is used for direct contact, fixation and positioning with skin during radioactive therapy. In order to meet the requirement of treatment accuracy, the existing stereotactic positioning stud needs to have certain strength, so that the stereotactic positioning stud and the components connected thereto are generally made of titanium alloy materials. Therefore, the stereotactic positioning stud is under an alternating magnetic field in a CT scan, and the inside of the stud generates a transient alternating current and generate heat. The temperature is too high to burn the patient's skin, which brings great harm to the patient.

Figure 1:
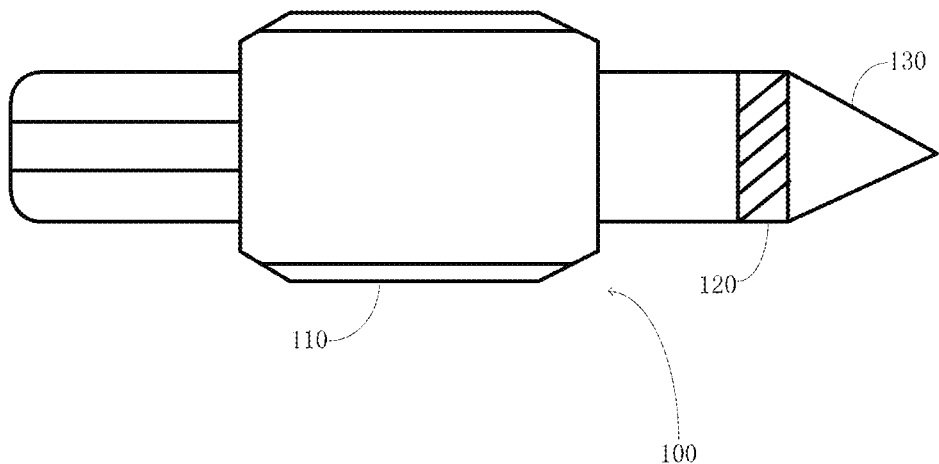
FIG. 1 is a schematic structural diagram of a positioning stud for radioactive therapy according to the present disclosure.
Figure 2:
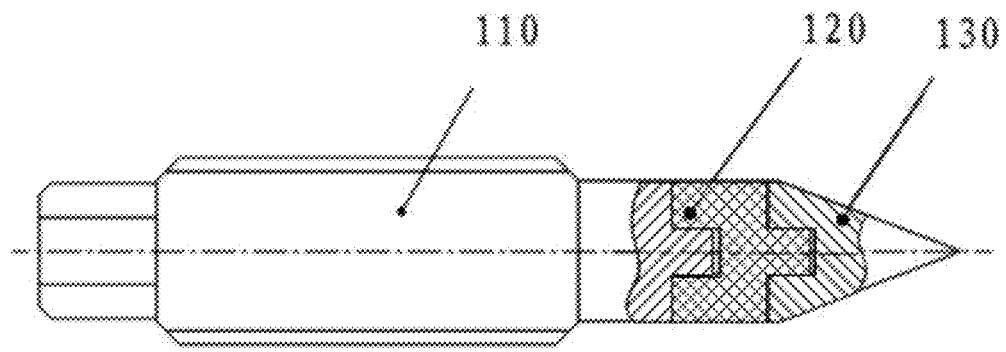
FIG. 2 is a schematic structural diagram of an embodiment of a connection of components for a positioning stud for radioactive therapy according to the present disclosure.
Figure 3:
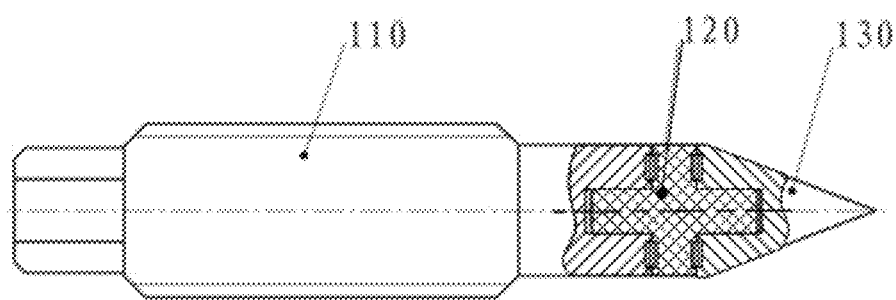
FIG. 3 is a schematic structural diagram of another embodiment of a connection of components for a positioning stud for radioactive therapy according to the present disclosure.
Figure 4:
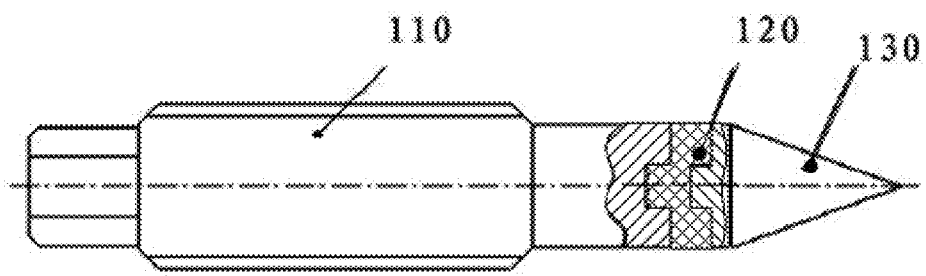
FIG. 4 is a schematic structural diagram of yet another embodiment of a connection of components for a positioning stud for radioactive therapy according to the present disclosure.

Referring FIGS. 1 to 4, FIG. 1 is a schematic structural diagram of a positioning stud for radioactive therapy according to the present disclosure; FIGS. 2 to 4 are schematic structural diagrams of a positioning stud for radioactive therapy using different types of insulating components according to the present disclosure.

The positioning stud 100 for radioactive therapy is typically used in radioactive therapy surgeries. In order to ensure that the rays emitted by the radiotherapy devices used in the surgeries accurately find the positions of patients' tumor tissues, it is necessary to fix the positions of the patients to be treated before performing precise radiotherapy. By performing a CT analog scan, image data of the patients may be accurately provided. The specific positions of the patients' lesions are marked, and the human body is accurately reconstructed by the three-dimensional coordinate system according to the image data, so that the rays can accurately irradiate to the targets, and the harm to other healthy parts of the patients are minimized.

Figure 8:
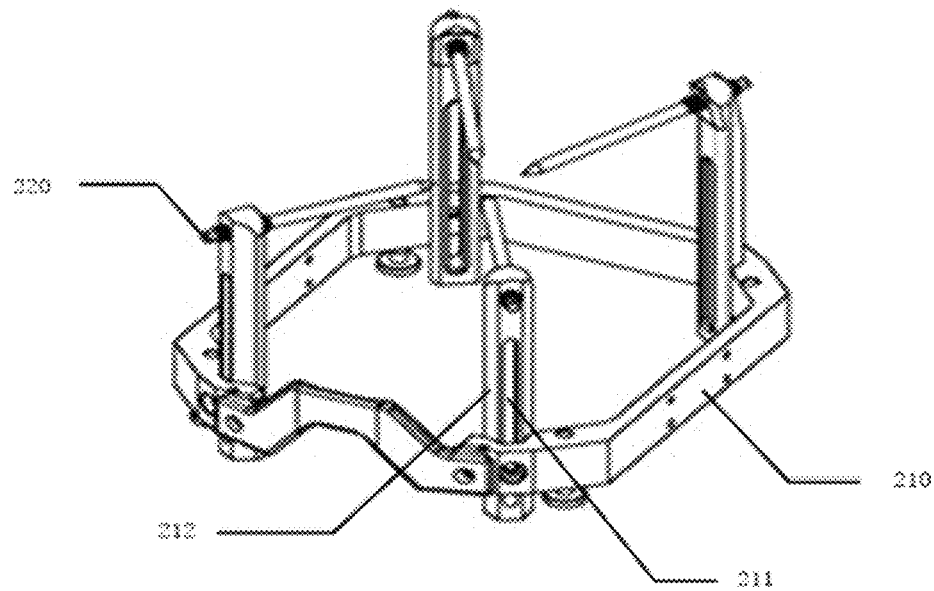
FIG. 8 is a schematic structural diagram of an embodiment of a stereotactic device according to the present disclosure.

Referring to FIG. 1, the positioning stud 100 according to the present disclosure includes a stud rod 110, an insulating component 120, and a stud tip 130. Referring to FIG. 8, the stud rod 110 is configured to connect to the stereotactic device 200. The stereotactic device (FIG. 8 shows a partial structure of the stereotactic device) is a device for fixing and positioning contours of the lesions on the surfaces of the patients to determine the positions of the rays irradiation after the three-dimensional coordinate system is reconstructed on the human body and the positions of the lesions are determined during the radioactive therapy. The stud tip 130 is in contact with the patients' skins for positioning the positions of the lesions. The stud tip 130 is usually set to a cone type. The bottom surface of the stub tip is connected to the insulating component 120, and the apex of the stub tip is in contact with the patients' skins. The insulating component 120 is connected between the stud rod 110 and the stud tip 130. The insulating component 120 can be an electrically insulating spacer having a certain thickness, and the electrically insulating spacer can be hollow or solid. The electrically insulating spacer is connected to a bottom surface of the cone-type stud tip 130 and a bottom surface of the cylinder-type stud rod 110. The stud tip 130 and the stud rod 110 are both made of titanium alloy materials. The electrically insulating spacer is disposed between the stud rod 110 and the stud tip 130 for blocking the connection between the stud rod 110 and the stud tip 120.

In the prior art, the stud tip 130 and the stud rod 110 of the positioning stud 100 are integrated. During the treatment process, as in the CT analog scan described above, a scanning apparatus applies an alternating magnetic field around the stereotactic device 200. Under the action of the alternating magnetic field, the positioning stud of titanium alloy generates heat due to the instantaneous alternating current generated by electromagnetic induction. The titanium alloy has excellent thermal conductivity, so that the stud tip may generate a higher temperature, which may cause damage to the patient's body surfaces when the stud tip is in contact with the patient's body surfaces, and the user experience is poor. However, in the present disclosure, the insulating component 120 is disposed between the stud tip 130 and the stud rod 110, at this time, the stud rod 110 generates heat due to the generation of the alternating current, but the current cannot be transmitted to the stud tip 130 due to the partition of the insulating component 120.

The temperature of the stud tip 130 is almost constant, so that the stub tip 130 does not cause damage to the patient's skins, which facilitates the continuous progress of the treatment process, and the user experience is high.

The electrically insulating spacer as the insulating component 120 is connected to the stud rod 110 by bonding, welding or plug-in type, and the electrically insulating spacer is connected to the stud tip 130 by bonding, welding or plug-in type. For example, the stud rod 110, the electrically insulating spacer and the stud tip 130 are sequentially bonded by using strong glue; or the stud rod 110, the electrically insulating spacer and the stud tip 130 are sequentially connected by welding. In addition, the surfaces on which the three are connected may be provided with raised steps and/or recess holes, and the connections are made by plug-in type.

As shown in FIGS. 2 to 4, a surface of the electrically insulating spacer as the insulating component 120 connected to the stud rod 110 is provided with the a recess hole, and a surface on the electrically insulating spacer that is connected to the stud tip 130 is provided with a raised step; in addition, a surface of the stud rod 110 connected to the electrically insulating spacer is correspondingly provided with a raised step, and a surface of the stud tip 130 connected to the insulating component 120 is correspondingly provided with a recess hole in FIG. 2. In FIG. 3, surfaces of the electrically insulating spacer as the insulating component 120 connected to the stud rod 110 and the stud tip 130 are provided with raised steps. In addition, the surface of the stud rod 110 connected to the electrically insulating spacer is provided with a recess hole correspondingly, and the surface of the stud tip 130 connected to the electrically insulating spacer is provided with a recess hole correspondingly. In FIG. 4, the surface of the electrically insulating spacer as the insulating component 120 connected to the stud rod 110 is provided with a raised step, and the surface on the electrically insulating spacer that is connected to the stud tip 130 is provided with a recess hole. In addition, the surface of the stud rod 110 connected to the electrically insulating spacer is provided with a recess hole correspondingly, and the surface of the stud tip 130 connected to the insulating component 120 is provided with a raised step correspondingly.

Figure 7:
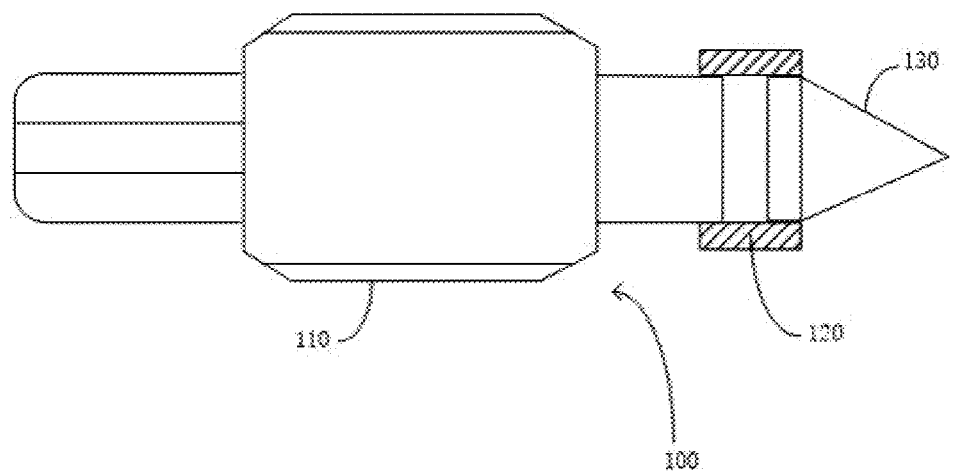
FIG. 7 is a schematic structural diagram of an embodiment of an insulating component of a positioning stud for radioactive therapy as a hollow pipe according to the present disclosure.

In other embodiments, as shown in FIG. 7, the electrically insulating spacer can be configured as a hollow pipe, the hollow pipe is made of insulating materials. Openings at two ends of the hollow pipe are provided with internal threads respectively, moreover, the positions where the stud rod 110 and the stud tip 130 are in contact with the electrically insulating spacer are provided with external threads for matching the internal threads of the hollow pipe, both the stud rod 110 and the stud tip 130 are connected to the electrically insulating spacer by a thread fit. The hollow pipe has a certain length, and after the stud rod 110 and the stud tip 130 are connected with the insulating component 120 by a thread fit, the stud rod 110 and the stud tip 130 are not in contact to prevent current or heat transferring between each other.

The above raised steps and the corresponding recess holes are connected by an interference fit. In the interference fits, the diameters of the matching shafts (shaft diameter of the raised steps) are generally greater than the diameters of the holes (aperture of the recessed holes), and which must be squeezed in with special tools, or by utilizing the characteristics of thermal expansion and contraction, the holes (recess holes) are heated, the diameters of the holes are enlarged, and the sleeves are quickly set in the shafts (raised steps), and the two are tightly integrated after being cooled and contracted.

In other embodiments, the raised steps can be provided with external threads, at the same time, the recess holes are provided with the internal threads correspondingly, the internal threads match with the external threads of the raised steps of the corresponding connecting surfaces, so that the connection among the stud rod 110, the electrically insulating spacer and the stud tip 130 are implemented by a thread fit of the raised steps and the recess holes. In the actual operation, after adopting interference fits or thread fits to realize connection, strong glue can be additionally used to bond, so that the connection of the three is firm.

The electrically insulating spacer is made of engineering materials of polyether-ether-ketone (PEEK), polyphenylene sulfone resins (PPSU) or ceramic. The above materials have high insulation and low thermal conductivity, which can minimize the heat conduct to the stud tip 130 and cause damage to the patients.

Figure 5:
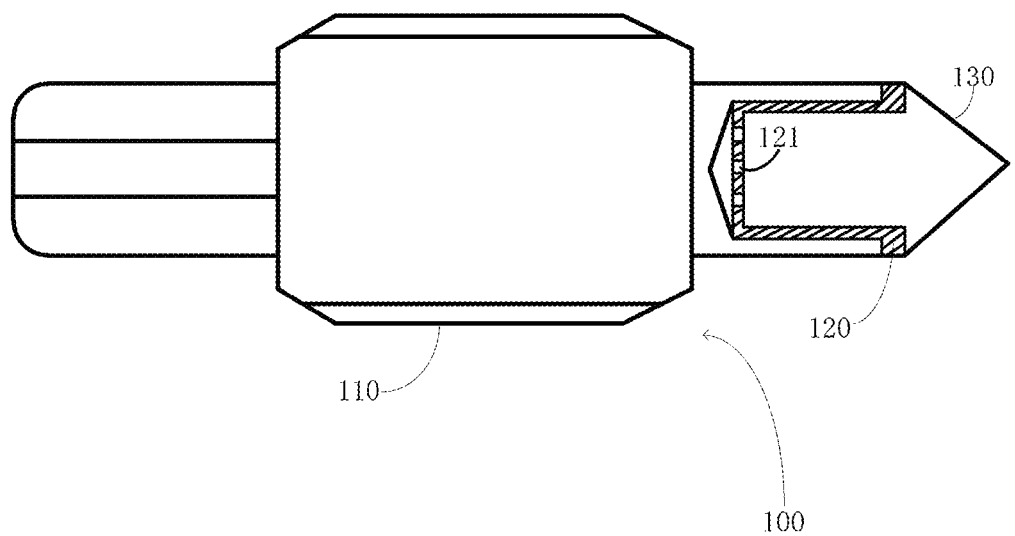
FIG. 5 is a schematic structural diagram of an embodiment of an insulating component of a positioning stud for radioactive therapy as an insulating sleeve according to the present disclosure.

In another embodiment of the present disclosure, as shown in FIG. 5, the insulating component 120 is an insulating sleeve. In the embodiment, one end of the stud rod 110 connected to the insulating component 120 is provided with the raised step and/or the recess hole, and one end of the stud tip 130 connected to the insulating component 120 is provided with the recess hole and/or the raised step correspondingly, and the raised step is cylindrical in shape, and the recess hole is a cylindrical hole that coincides with the raised step.

Referring to FIG. 5, taking one end of the stud rod 110 in contact with the insulating component 120 is provided with the recess hole, and one end of the stud tip 130 in contact with the insulating component 120 is provided with the raised step as an example, the insulating sleeve is sleeved on the raised step provided at one end of the stud tip 130. After the insulating sleeve is sleeved on the raised step, the raised step with the insulating sleeve is fixedly connected with the recess hole disposed at one end of the stud rod 110 by an interference fit. Alternatively, an outer surface of the insulating sleeve is provided with external thread, and a recess hole disposed at one end of the stud rod 110 is provided with internal threads; moreover, an inner surface of the insulating sleeve is provided with internal threads, and the outside of the raised step disposed at one end of the stud tip 130 is provided with internal threads, and the raised step, the recess hole and the insulating component 120 are fixedly connected by an thread fit. Alternatively, the raised step, the recess hole and insulating component 120 may be fixedly connected by strong glue. In a case where the insulating sleeve is sleeved on the raised step, since the insulating sleeve is tightly combined with the raised step, the raised step may compress the air at the bottom of the insulating sleeve, and in a case where the positioning stud 100 is in a high temperature environment, the gas is thermally expanded, which may possibly cause the connection position of the raised step and the insulating sleeve to move. Therefore, the bottom of the insulating sleeve is provided with a vent hole 121, so that the air in the insulating sleeve is discharged when the raised step is set on the insulating sleeve.

Figure 6:
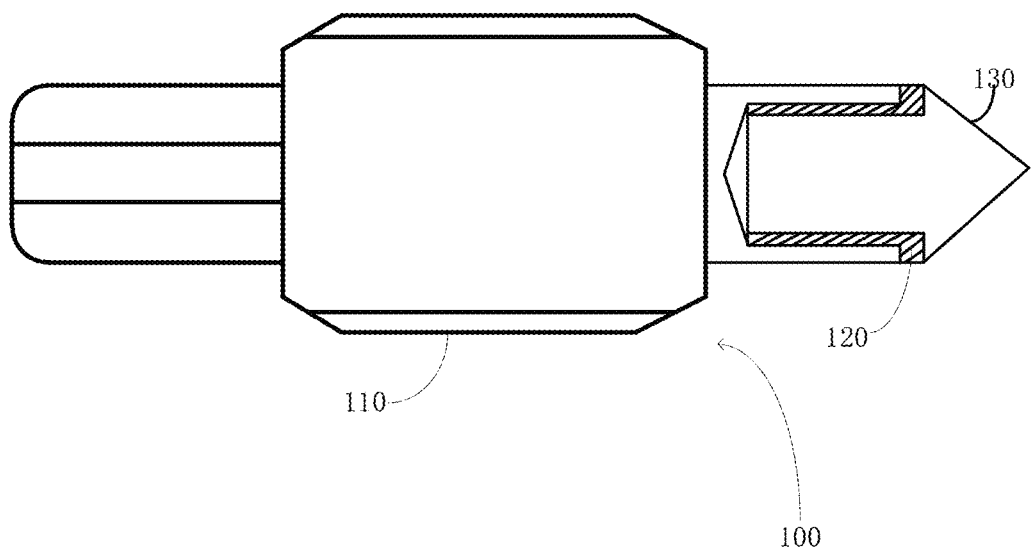
FIG. 6 is a schematic structural diagram of an embodiment of an insulating component of a positioning stud for radioactive therapy as a sleeve according to the present disclosure.

In another embodiment of the present invention, as shown in FIG. 6, the insulating component 120 is a sleeve. In still another alternative mode, the axial length of the sleeve is greater than the axial length of the raised step to prevent the raised step of the stud tip 130 from contacting the recess hole of the stud rod 110 to conduct heat. In a case where the stereotactic device 200 is in a magnetic field environment, the positioning stud 100 is connected to the stereotactic device 200, and the stereotactic device 200 generates an instantaneous strong current under the action of the magnetic field. However, by providing an insulated sleeve, when the stud rod 110 and the stud tip 130 are connected by the insulation of the sleeve, the stud tip 130 does not generate high temperature due to the action of current, which does not cause harm to patients.

Different from the prior art, the positioning stud 100 for radioactive therapy of the present disclosure includes a stud rod 110, a stud tip 130, and an insulating component 120; the insulating component is connected between the stud rod 110 and the stud tip 130, and is configured to prevent contact between the stud rod 110 and the stud tip 130. According to the present disclosure, it is possible to prevent the stud tip 130 from scalding the skin of a patient when the temperature of the stud tip 130 is too high due to the hear caused by an alternating current generated by the effect of an alternating magnetic field, thereby guaranteeing the safety of the therapy process.

Referring to FIG. 8, FIG. 8 is a schematic structural diagram of an embodiment of a stereotactic device 200 according to the present disclosure. The stereotactic device 200 includes a positioning connection frame 210 and at least two positioning studs 220 as described in the previous embodiments. The structure of the positioning stud 220 is similar or even the same as that of the positioning stud 100 described in the previous embodiments, which will not be described herein again.

The positioning connection frame 210 is generally configured to a ring structure and is made of metal material. The frame of the positioning connection frame 210 is configured to be a square or a circular, and the side length or the diameter of the frame can be changed according to the lesion sizes of the treatment subjects. In the present embodiment, the positioning connection frame 210 is configured to a square frame. The position of each right angle of the square is fixedly provided with a positioning stud 100, and the stereotactic device 200 includes four positioning studs 100. The position of each right angle of the positioning connection frame 210 of the square structure are provided with a slide rails 211, the slide rails 211 are provided with slide blocks 212, and the slide blocks 212 are movable on the slide rails 211 in a direction perpendicular to the plane of the square positioning connection frame 210. One ends of the slide blocks 212 is provided with screw holes, and the screw holes are provided with internal threads, and the internal threads can match with the external threads provided on the stud rods of the positioning studs 220 to fix the positioning studs 220 to the positioning connection frame 210. The stud rods of the positioning studs 220 are connected to the positioning connection frame 210 by a thread fit or by nylon fibulae, and the structures are generally configured to cylinder types. For example, the outer sides of the stud rods are provided with external threads, and positions where the positioning connection frame 210 is connected to the stud rods are provided with internal threads corresponding to the external threads, and the positioning studs 220 are connected to the positioning connection frame 210 by thread fits.

During the treatment process, the square ring structure of the positioning connection frame 210 is sleeved on the lesion position, such as a head or an arm, and the positioning studs 220 can reach a proper position by adjusting the positions of the slide blocks 212 to contact to patients' skins for subsequent radioactive therapy.

Different from the prior art, the stereotactic device 200 of the present disclosure includes the positioning connection frame 210, and the two positioning studs 220 according to the foregoing technical solution, each positioning stud 220 is fixedly connected to the positioning connection frame 210. According to the present disclosure, it is possible to prevent the stud tip from scalding the skin of a patient when the tip temperature is too high due to the heat caused by the alternating current generated by the effect of the alternating magnetic field, thereby guaranteeing the safety of the therapy process.

The above description is only embodiments of the present disclosure, and thus does not limit the patent scope of the present disclosure. Any equivalent structure or equivalent process transformation, or directly or indirectly used in other related technical fields by the specification and the drawings content of the present disclosure, are all comprised in the scope of patent protection of the present disclosure.

What is claimed is:

1. A positioning stud for radioactive therapy, comprising:
   a stud rod, a stud tip, and an insulating component; and
   the insulating component being connected between the stud rod and the stud tip, and being configured to prevent contact between the stud rod and the stud tip.

2. The positioning stud for radioactive therapy according to claim 1, wherein the insulating component is an electrically insulating spacer.

3. The positioning stud for radioactive therapy according to claim 2, wherein the electrically insulating spacer is connected to the stud rod by bonding, welding or plug-in type, and the electrically insulating spacer is connected to the stud tip by bonding, welding or plug-in type.

4. The positioning stud for radioactive therapy according to claim 2, wherein
   each of two opposite surfaces of the electrically insulating spacer are provided with a first connecting portion,
   a surface of the stud rod connected to the electrically insulating spacer is provided with a second connecting portion correspondingly, and a surface of the stud tip connected to the electrically insulating spacer is provided with a second connecting portion correspondingly, and
   the second connecting portion on the stud rod is connected to a corresponding first connecting portion on the electrically insulating spacer, and the second connecting portion on the stud tip is connected to a corresponding first connecting portion on the electrically insulating spacer.

5. The positioning stud for radioactive therapy according to claim 4, wherein the first connecting portion is a raised step and/or a recess hole, and the second connecting portion is a corresponding recess hole and/or a corresponding raised step.

6. The positioning stud for radioactive therapy according to claim 5, wherein the raised step is inserted into the recess hole by an interference fit for their connection.

7. The positioning stud for radioactive therapy according to claim 5, wherein the raised step is provided with external threads, and the recess hole is provided with internal threads for matching with the external threads of the raised step, and the raised step and the recess hole are connected by a thread fit.

8. The positioning stud for radioactive therapy according to claim 1, wherein the insulating component is an insulating sleeve or a sleeve;
   one end of the stud rod in contact with the insulating component is provided with a raised step or a recess hole, and one end of the stud tip in contact with the insulating component is provided with a recess hole or a raised step correspondingly; and the insulating component is sleeved on the raised step, and the raised step sleeved on the insulating component is connected to the recess hole.

9. The positioning stud for radioactive therapy according to claim 8, wherein the raised step sleeved on the insulating component is connected to the recess hole by interference fit; or, an outer side of the insulating component is provided with external threads, and the recess hole disposed on the stud rod or the stud tip is provided with internal threads, and the stud rod or the stud tip is connected to the insulating sleeve by a thread fit; an inner side of the insulating component is provided with internal threads, and the raised step disposed on the stud rod or the stud tip is provided with external threads, and the insulating component is connected to the raised step by a thread fit.

10. The positioning stud for radioactive therapy according to claim 1, wherein an outer side of the stud rod is provided with a connecting member for connection to a stereotactic device.

11. The positioning stud for radioactive therapy according to claim 1, wherein the insulating component is made of one of engineering materials of polyether-ether-ketone, polyphenylene sulfone resins or ceramic.

12. A stereotactic device, comprising:
a positioning connection frame,
at least two positioning studs according to claim 1, wherein the at least two positioning studs are fixedly connected to the positioning connection frame.

13. The stereotactic device according to claim 12, wherein the positioning connection frame includes at least two sliding rails having a same number as the at least two positioning studs, each sliding rail is vertically disposed on a plane of the positioning connection frame, each sliding rail is connected to a sliding block which is able to slide along the sliding rail, and each positioning stud is fixedly connected to a corresponding sliding block.

14. The stereotactic device according to claim 12, wherein an outer side of the stud rod is provided with a connecting member, and the connecting member is provided with external threads, and a position where the stereotactic device is connected to the positioning stud is provided with internal threads, and the connecting member connects the positioning stud and the stereotactic device by a thread fit.

15. The stereotactic device according to claim 12, wherein an outer side of the stud rod is provided with a connecting member, and the connecting member is a velvet strip or a hook strip of Velcro, and a position where the stereotactic device is connected to the positioning stud is provided with a corresponding hook strip or a corresponding velvet strip of Velcro, so that the positioning stud is connected to the stereotactic device.

16. The positioning stud for radioactive therapy according to claim 1, wherein the electrically insulating spacer is configured as a hollow pipe;

openings at two ends of the hollow pipe are provided with internal threads respectively, and positions where the stud rod and the stud tip are in contact with the electrically insulating spacer are provided with external threads for matching the internal threads of the hollow pipe; and both the stud rod and the stud tip are connected to the electrically insulating spacer by a thread fit.

* * * * *